(12) United States Patent
Kerkow et al.

(10) Patent No.: US 11,129,945 B2
(45) Date of Patent: Sep. 28, 2021

(54) AUTO-INJECTOR DEVICE

(71) Applicant: Sanofi-Aventis Deutschland GMBH, Frankfurt am Main (DE)

(72) Inventors: Daniel Kerkow, Frankfurt am Main (DE); Florian Schauderna, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 314 days.

(21) Appl. No.: 16/307,023

(22) PCT Filed: May 31, 2017

(86) PCT No.: PCT/EP2017/063087
§ 371 (c)(1),
(2) Date: Dec. 4, 2018

(87) PCT Pub. No.: WO2017/211628
PCT Pub. Date: Dec. 14, 2017

(65) Prior Publication Data
US 2019/0217024 A1    Jul. 18, 2019

(30) Foreign Application Priority Data

Jun. 6, 2016    (EP) .................................... 16173153

(51) Int. Cl.
*A61M 5/42*    (2006.01)
*A61M 5/20*    (2006.01)
*A61M 5/32*    (2006.01)

(52) U.S. Cl.
CPC .............. *A61M 5/425* (2013.01); *A61M 5/20* (2013.01); *A61M 5/2033* (2013.01);
(Continued)

(58) Field of Classification Search
CPC ...... A61M 5/425; A61M 5/20; A61M 5/2033; A61M 5/3202; A61M 2005/3246; A61M 2005/3258; A61M 2205/3344
See application file for complete search history.

(56) References Cited

U.S. PATENT DOCUMENTS 4,299,219 A     11/1981  Norris
2002/0170557 A1*  11/2002  Schmidt ................ A61M 16/06
                                                    128/200.23
(Continued)

FOREIGN PATENT DOCUMENTS

CN    101869734      10/2010
JP    H08-508901     9/1996
(Continued)

OTHER PUBLICATIONS

International Preliminary Report on Patentability in International Application No. PCT/EP2017/063087, dated Dec. 11, 2018, 9 pages.

(Continued)

*Primary Examiner* — Manuel A Mendez
*Assistant Examiner* — Justin L Zamory
(74) *Attorney, Agent, or Firm* — Fish & Richardson P.C.

(57) ABSTRACT

An auto-injector device comprising an injector body having a proximal end and a distal end; a syringe received in the injector body; a needle disposed in a first end of the syringe to extend toward an opening in the distal end of the injector body; and a sealing element disposed at the distal end of the injector body for making a seal against a patient's skin. The auto-injector is configured to generate a reduced pressure to draw the auto-injector device against the patient's skin. The auto-injector device comprises a pressure-reducing mechanism configured to generate the reduced pressure within the injector body during an injection process. The pressure reducing mechanism comprises a moveable member con- (Continued)

figured such that movement of the moveable member from a first position to a second position enlarges a closed volume within the injector body to generate the reduced pressure within the closed volume.

20 Claims, 6 Drawing Sheets

(52) U.S. Cl.
CPC ... *A61M 5/3202* (2013.01); *A61M 2005/3246* (2013.01); *A61M 2005/3258* (2013.01); *A61M 2205/3344* (2013.01)

(56) References Cited

U.S. PATENT DOCUMENTS

| | | | |
|---|---|---|---|
| 2003/0093032 A1* | 5/2003 | Py | A61M 5/425 604/117 |
| 2005/0033234 A1* | 2/2005 | Sadowski | A61M 5/2033 604/140 |
| 2007/0088348 A1 | 4/2007 | Kochamba | |
| 2007/0270745 A1 | 11/2007 | Nezhat et al. | |
| 2008/0039795 A1 | 2/2008 | Slate et al. | |

FOREIGN PATENT DOCUMENTS

| | | |
|---|---|---|
| JP | 2003-533293 | 11/2003 |
| JP | 2005-516737 | 6/2005 |
| JP | 2009-538217 | 11/2009 |
| JP | 2014-532524 | 12/2014 |
| WO | WO 1994/023777 | 10/1994 |
| WO | WO 2001/087389 | 11/2001 |
| WO | WO 2007/138349 | 12/2007 |
| WO | WO 2013/070715 | 5/2013 |

OTHER PUBLICATIONS

International Search Report and Written Opinion in International Application No. PCT/EP2017/063087, dated Aug. 31, 2017, 13 pages.

* cited by examiner

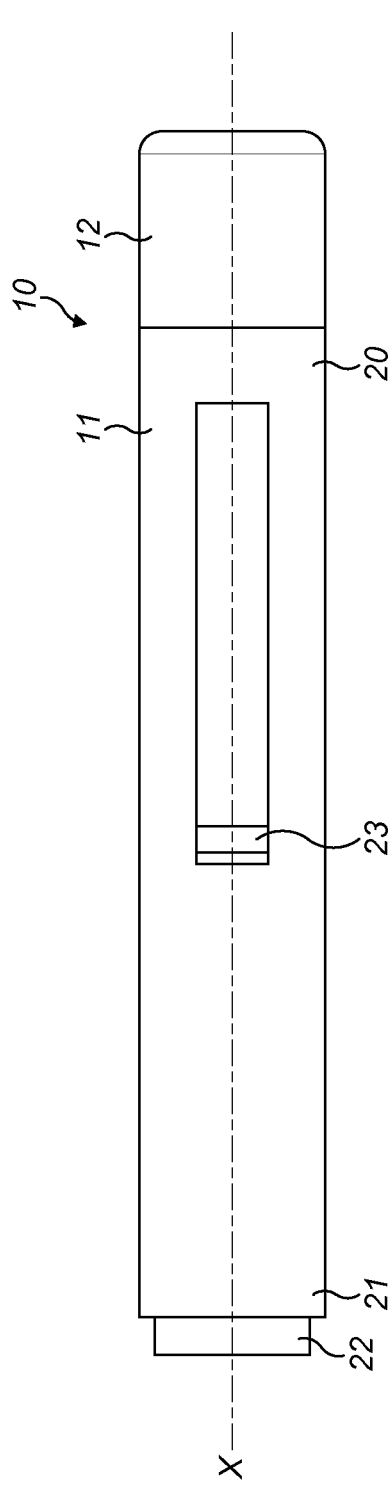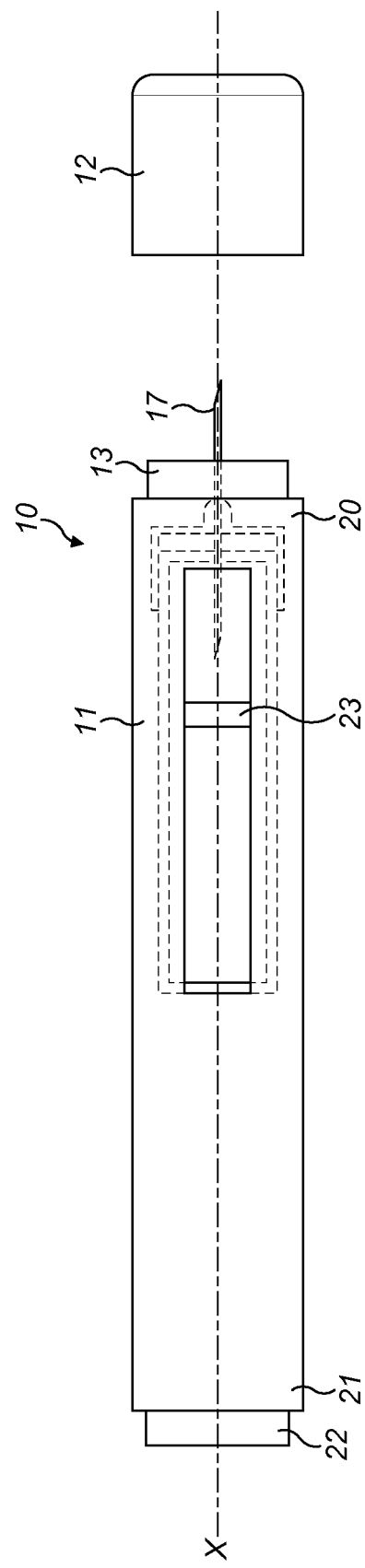
FIG. 1A
FIG. 1B

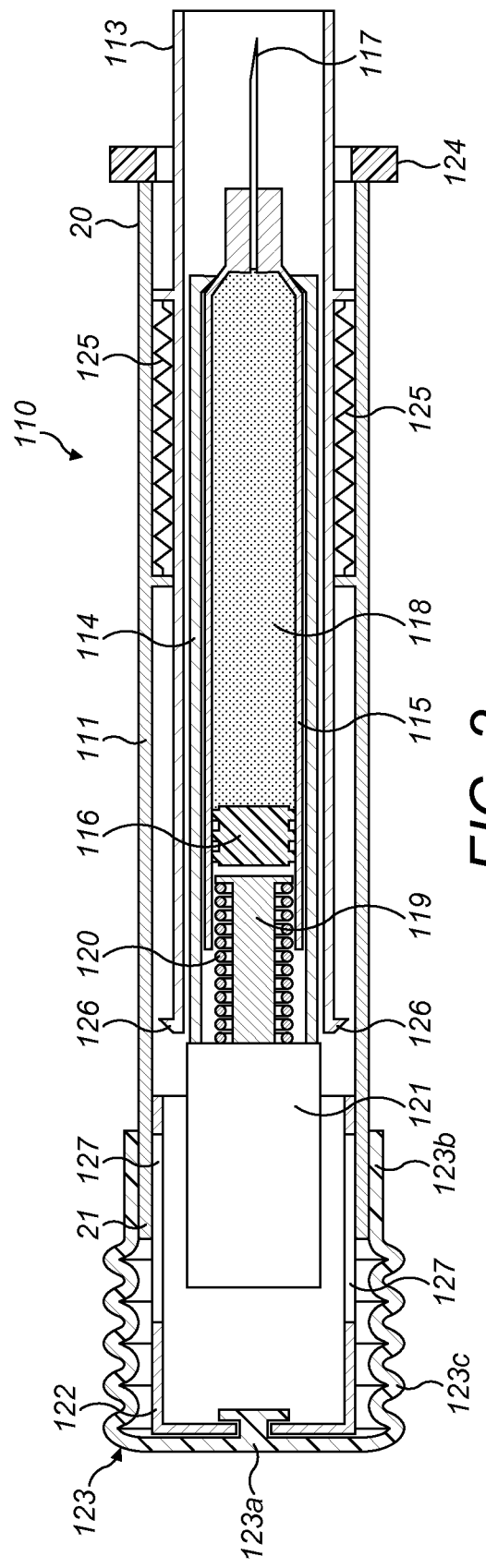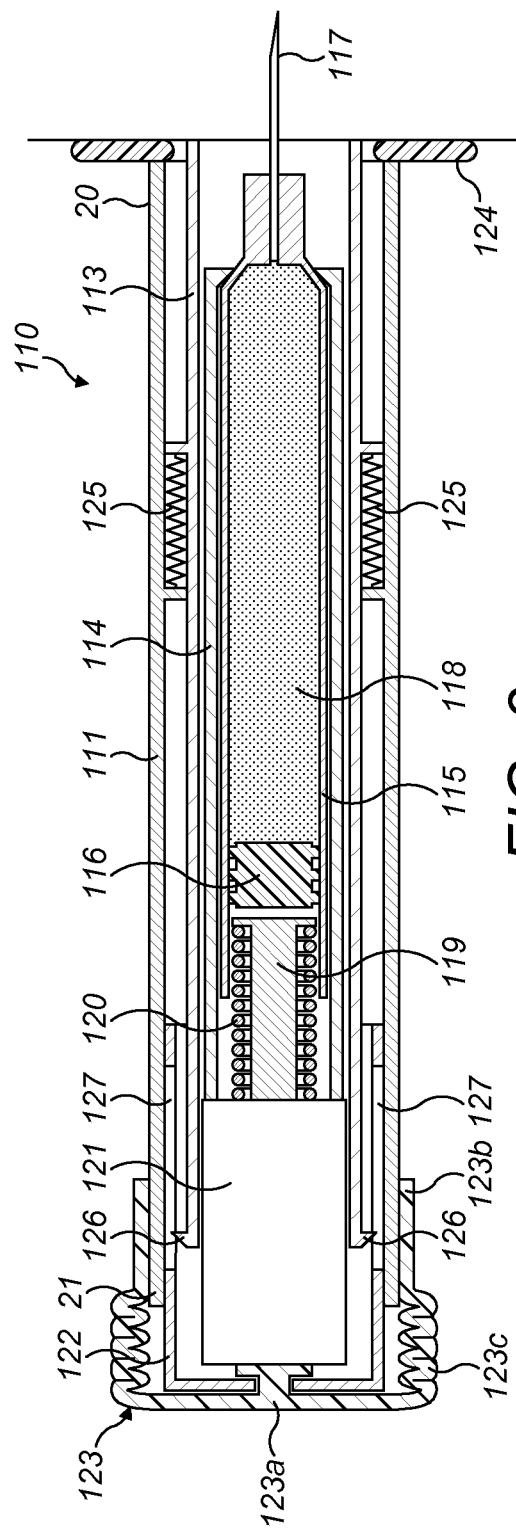

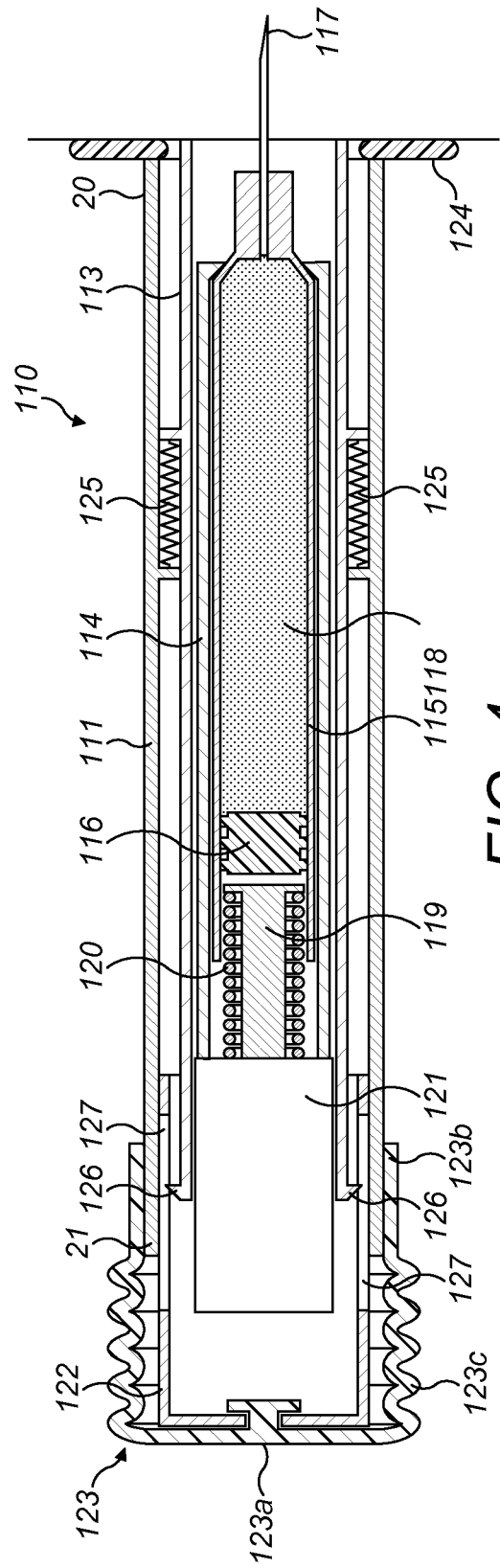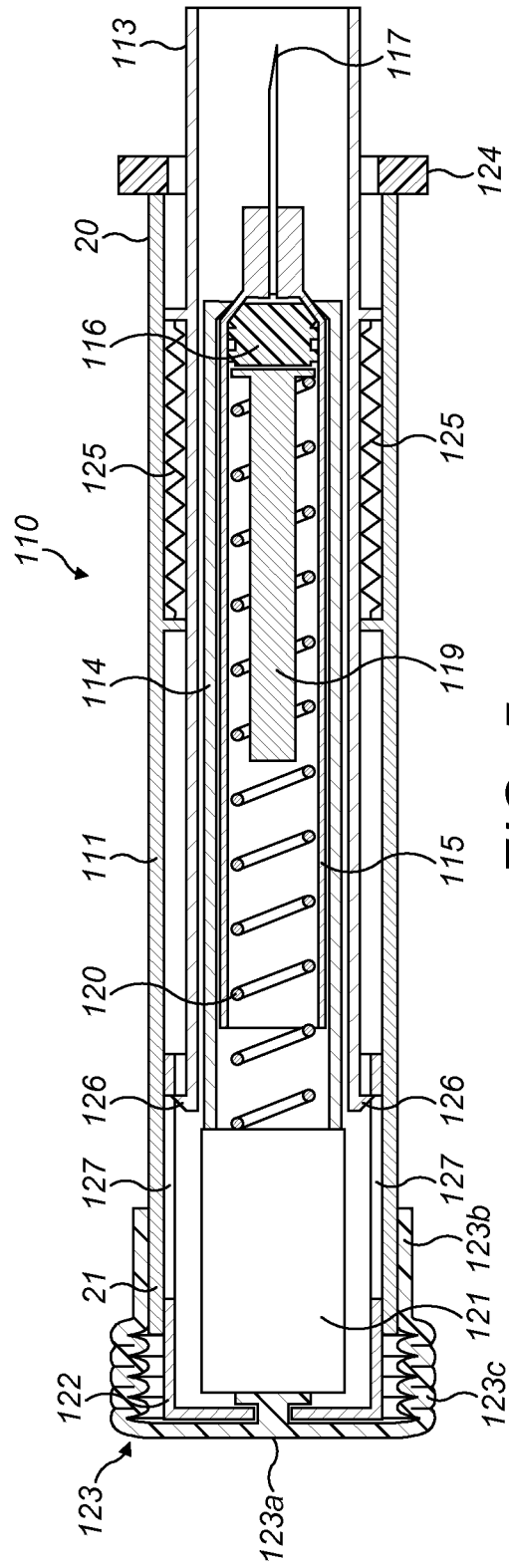

AUTO-INJECTOR DEVICE

CROSS REFERENCE TO RELATED APPLICATIONS

The present application is the national stage entry of International Patent Application No. PCT/EP2017/063087, filed on May 31, 2017, and claims priority to Application No. EP 16173153.4, filed on Jun. 6, 2016, the disclosures of which are incorporated herein by reference.

TECHNICAL FIELD

This application relates to an injector drug delivery device.

BACKGROUND

Injector devices are used to deliver a range of liquid medicaments. These devices have application where regular injections by persons without formal medical training occur. This is common among patients where self-treatment enables effective management of their disease.

Correct use of an injector device by the patient is essential to ensure effective treatment of the respective medical condition. Such correct use includes ensuring the injection step occurs properly and the complete medicament dose is injected into the patient. It is advantageous to make the medicament delivery process straight-forward and intuitive for the patient to complete themselves. Incomplete or incorrect use of the injector device can result in ineffective treatment of the medical condition and potentially injury or discomfort to the patient.

SUMMARY

According to a first aspect there is provided an auto-injector device for delivering a liquid medicament, comprising an injector body having a proximal end and a distal end, a syringe received in the injector body, a needle disposed in a first end of the syringe to extend toward an opening in the distal end of the injector body, and a sealing element disposed at the distal end of the injector body for making a seal against a patient's skin and thereby define a closed volume within the injector body in use, wherein the auto-injector is configured to generate a reduced pressure within the closed volume to draw the auto-injector device against the patient's skin, and wherein the auto-injector device comprises a pressure-reducing mechanism configured to generate the reduced pressure within the injector body during an injection process, the pressure reducing mechanism comprising a moveable member configured such that movement of the moveable member from a first position to a second position enlarges the closed volume within the injector body to generate the reduced pressure within the closed volume, and wherein the moveable member is biased into the second position.

The syringe may include a second end opposite the first end, wherein the second end is open and in fluid communication with the closed volume within the injector body, and wherein the pressure reducing mechanism comprises the syringe.

The auto-injector device may further comprise a needle sleeve moveable between an extended position in which the needle sleeve extends from the distal end of the injector body and surrounds the needle, and a retracted position in which the needle sleeve is retracted into the injector body to expose the needle.

The auto-injector device may further comprise a holding mechanism configured to hold the moveable member in the first position and to release the moveable member when the needle sleeve moves from the extended position to the retracted position.

The needle sleeve may include a first coupling element and the moveable member may include a second coupling element, and wherein the first and second coupling elements engage when the needle sleeve moves to the retracted position.

The injector body may include a non-return valve configured to allow air to flow out of the injector body but prevent air flowing into the injector body from outside the device.

The sealing element may comprise a resilient annular sealing member disposed around a rim of the injector body at the distal end.

The auto-injector device may comprise a release element operable to equalise the reduced pressure within the closed volume with air pressure outside the injector body.

The release element may comprise a release valve, and the auto-injector device may further comprise a release mechanism configured to automatically operate the release valve when a medicament delivery process is complete.

The release element may be manually operable to allow a user to actuate the release element.

The syringe may contain a liquid medicament or a cartridge of liquid medicament.

According to a second aspect, there is provided a method of operation of an auto-injector device for delivering a liquid medicament comprising an injector body having a proximal end and a distal end, a syringe received in the injector body, a needle disposed in a first end of the syringe to extend toward an opening in the distal end of the injector body, a sealing element disposed at the distal end of the injector body, and a pressure-reducing mechanism comprising a moveable member moveable from a first position to a second position and biased into the second position, the method comprising placing the distal end of the injector body against a patient's skin, making a seal between the injector body and the patient's skin with the sealing element and thereby defining a closed volume within the injector body, and the moveable member moving from the first position to the second position to enlarge the closed volume within the injector body and thereby generating a reduced pressure within the closed volume to draw the auto-injector device against the patient's skin.

BRIEF DESCRIPTION OF THE DRAWINGS

So that the present disclosure may be more fully understood, embodiments will now be described, by way of examples only, with reference to the accompanying drawings in which:

FIG. 1A shows an auto injector with a cap attached;

FIG. 1B shows the auto injector of FIG. 1A with the cap removed;

FIG. 2 shows an auto injector according to a first embodiment of the invention in a configuration prior to an injection process;

FIG. 3 shows the auto injector of FIG. 2 in a first configuration during an injection process;

FIG. 4 shows the auto injector of FIG. 2 in a second configuration during an injection process;

FIG. 5 shows the auto injector of FIG. 2 in a configuration after an injection process;

DETAILED DESCRIPTION

Figure 6:
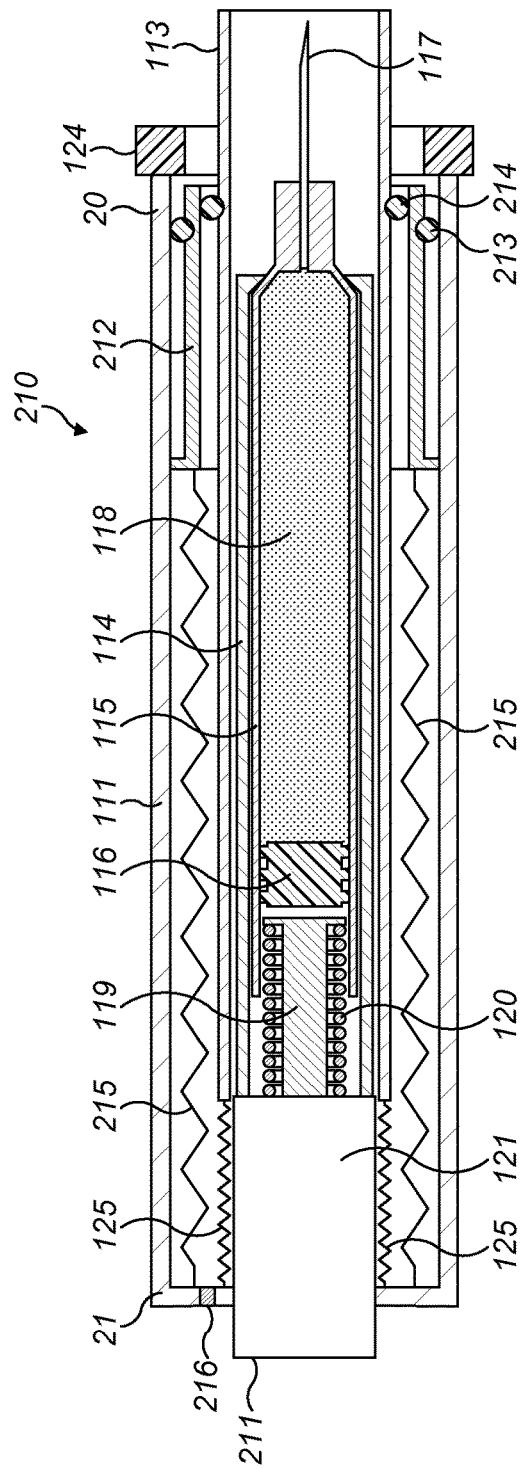
FIG. 6 shows an auto injector according to a second embodiment of the invention in a configuration prior to an injection process.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17. Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Referring now to FIGS. 2 to 5, an auto injector 110 according to a first embodiment is shown comprising an injector housing body 111 (hereafter "body") having a distal region 20 and a proximal region 21. A needle sleeve 113 is provided within the body 111 and is slidable relative to body 111 between an extended position (shown in FIGS. 2 and 5) and a retracted position (shown in FIGS. 3 and 4). The needle sleeve 113 is a generally tubular structure.

A syringe holder 114 is disposed within the needle sleeve 113 and is configured to receive a syringe 115 or cartridge of liquid medicament 118. Alternatively, the syringe 115 may be configured to receive a cartridge of liquid medicament 118. The syringe 115 includes a needle 117 at one end and disposed at the distal end 20 of the body 111. The needle 117 extends beyond the distal end 20 of the body. The needle sleeve 113 surrounds the needle 117 in its extended position and the needle 117 is exposed when the needle sleeve 113 is moved to its retracted position.

The syringe 115 includes a stopper 116 at an opposite end to the needle 117 which seals against an inside wall of the syringe 115 to retain the liquid medicament 118 inside the syringe 115. A plunger 119 is disposed adjacent the stopper 116 to move the stopper 116 within the syringe 115 to expel the medicament 118 out of the needle 117. A plunger spring 120 is provided around the plunger 119 and acts to bias the plunger 119 in a direction towards the stopper 116. A power pack 121 (only shown schematically in FIGS. 2 to 5) is connected to the plunger 119 to drive the plunger 119 in a direction towards the stopper 116 assisted by the plunger spring 120.

The proximal end 21 of the body 111 is closed by a moveable member in the form of a cylindrical cover 122. The cylindrical cover 122 is slidably received in the proximal end 21 of the body 111. A flexible cap 123 is disposed over the cover 122 and includes a flat end portion 123a which is connected to the cover 122, and a skirt portion 123b which is secured to the body 111. The flexible cap 123 thereby makes an air-tight seal over the proximal end 21 of the body 111. The body 111 is open at the distal end 20 but does not include any other passages along its length through which air can freely flow. Accordingly, if the distal end 20 of the body 111 is sealed closed, a sealed closed volume is defined within the body 111.

The flexible cap 123 includes a spring section 123c between the flat end 123a and the skirt 123b. The spring section 123c is configured to allow the flexible cap to deform between an expanded state (shown in FIGS. 2 and 4) and a compressed state (shown in FIGS. 3 and 5). The spring section 123c is configured to bias the flexible cap 123 into the expanded state. This may be by virtue of the resilient property of the material from which the flexible cap 123 is made, such as rubber. Alternatively, or in addition, the flexible cap 123 may include an additional spring element (not shown) secured to or embedded within the body of the flexible cap 123.

The distal end 20 of the body 111 includes a sealing member 124 in the form of an annular element secured around the end rim of the body 111.

Sleeve springs 125 are provided which bias the needle sleeve 113 into the extended position. The sleeve springs 125 are connected to an inward projection extending from an inner wall of the body 11 and an outward projection extending from an outer wall of the needle sleeve 113. One or a plurality of sleeve springs 125 may be provided, and the inward and outward projections may comprise an annular flange or a plurality of discrete projections extending from around the periphery of the body 111 and needle sleeve 113 respectively.

An end of the needle sleeve 113 near the proximal end 21 of the body 111 includes a first coupling element in the form of a hook 126 with a ramped face facing a direction towards the proximal end 21 of the body 111 and a radial face facing in a direction towards the distal end 20 of the body 111. The cover 122 includes a second coupling element in the form of an aperture 127 aligned with the hook 126.

Operation of the auto injector 110 of the first embodiment will now be described. The auto injector 110 is initially in configuration shown in FIG. 2, in which the needle sleeve 113 is in the extended position. The distal end 20 of the auto injector 110 is pressed against the injection site on a patient's body. The needle sleeve 113 slides from the extended position to the retracted position inside the body 111, compressing the sleeve springs 125. The needle 117 is thereby exposed and pierces the patient's skin and the sealing member 124 creates an air-tight seal against the patient's skin around the injection site. As the distal end 20 of the body 111 is thereby sealed closed by the sealing member 124 and the patient's skin, a sealed closed volume is thereby defined within the body 111. The sealing member 124 may be deformable as indicted by the change of shape of the sealing member 124 shown in FIGS. 2 and 3, to help achieve an effective seal against the patient's skin. The patient then pushes the flat end portion 123a of the flexible cap 123 which causes the spring section 123c to deform into the compressed state and the cover 122 to slide into the body 111. This increase in air pressure within the body 111 causes air to be expelled from within the body 111 past the sealing member 124. In an alternative configuration, the body 111 may include a non-return valve to allow air to flow out of the body to atmosphere when the pressure within the body 111 rises above ambient air pressure outside the body 111. The non-return valve would prevent air flowing back into the body 111 when the pressure within the body 111 is lower than ambient atmospheric pressure outside the body 111. The ramped face of the hook 126 rides over the distal end of the cover 122 and the hook 126 locates in the aperture 127. The auto injector is thereby in the configuration shown in FIG. 3.

Once in the configuration shown in FIG. 3, the spring section 123c is urged to return to its expanded state by virtue of the resilient property of the material from which the flexible cap 123 is made and/or any additional spring element (not shown). This configuration is shown in FIG. 4. This enlarges the closed volume within the body 111 and results in a reduced pressure relative to ambient pressure, within the closed volume define by the body 111. The resulting suction effect draws auto injector 110 against the patient's skin and helps support the auto injector 110 in position.

The cover 122 having previously contacted and activated the power pack 121 when the auto injector 110 was in the configuration shown in FIG. 3, causes the plunger 119 to be actuated to drive the stopper 116 to deliver the medicament 118 into the patient.

Once the medicament delivery operation is completed, the patient removes the auto-injector 110 from their skin. This can be achieved by the patient pushing the flat end portion 123a of the flexible cap 123 which causes the spring section 123c to deform into the compressed state and the cover 122 to slide into the body 111. This reduces the closed internal volume within the body 111 and thereby reduces the extent of the reduced pressure therein, and so reduces the suction effect of the auto injector 110 on the patient's skin. The needle sleeve 113 then slides into the extended position under the force of the sleeve springs 125 to surround the needle 117. The hooks 126 engage with the edges of the apertures 127 in the cover 122 and draws the cover 122 into its compressed position also under the force provided by the sleeve springs 125.

Figure 7:
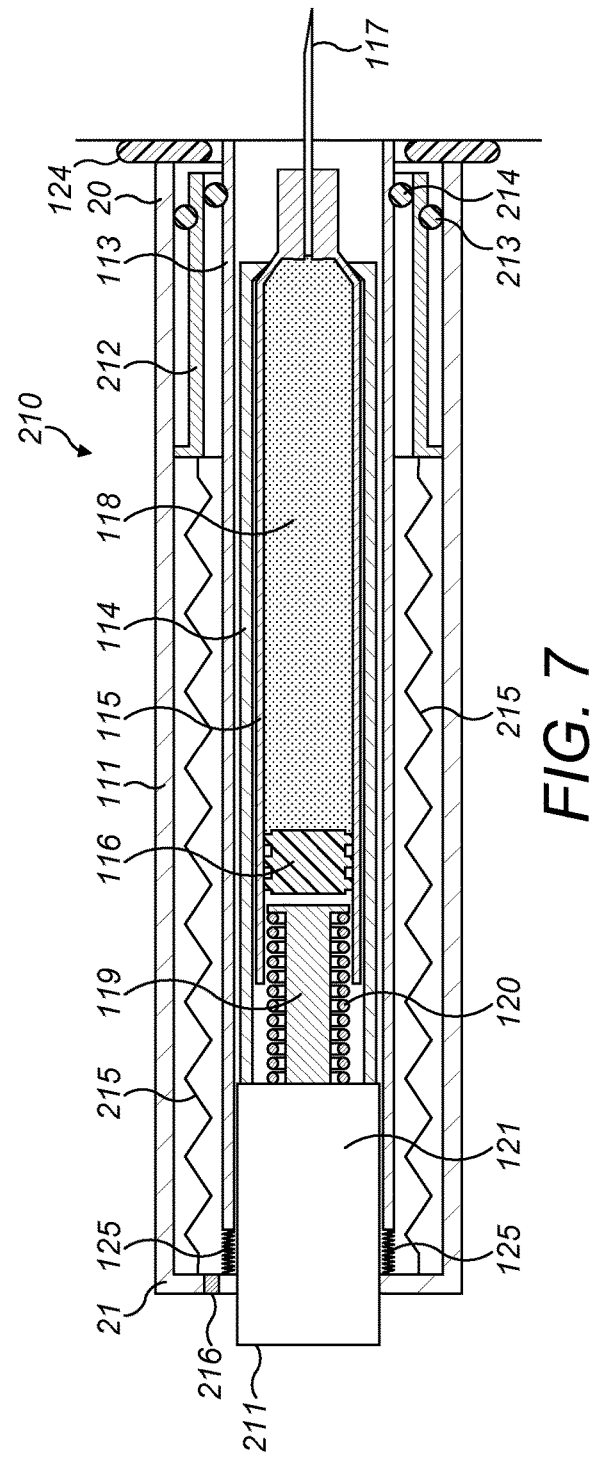
FIG. 7 shows the auto injector of FIG. 6 in a first configuration during an injection process.
Figure 8:
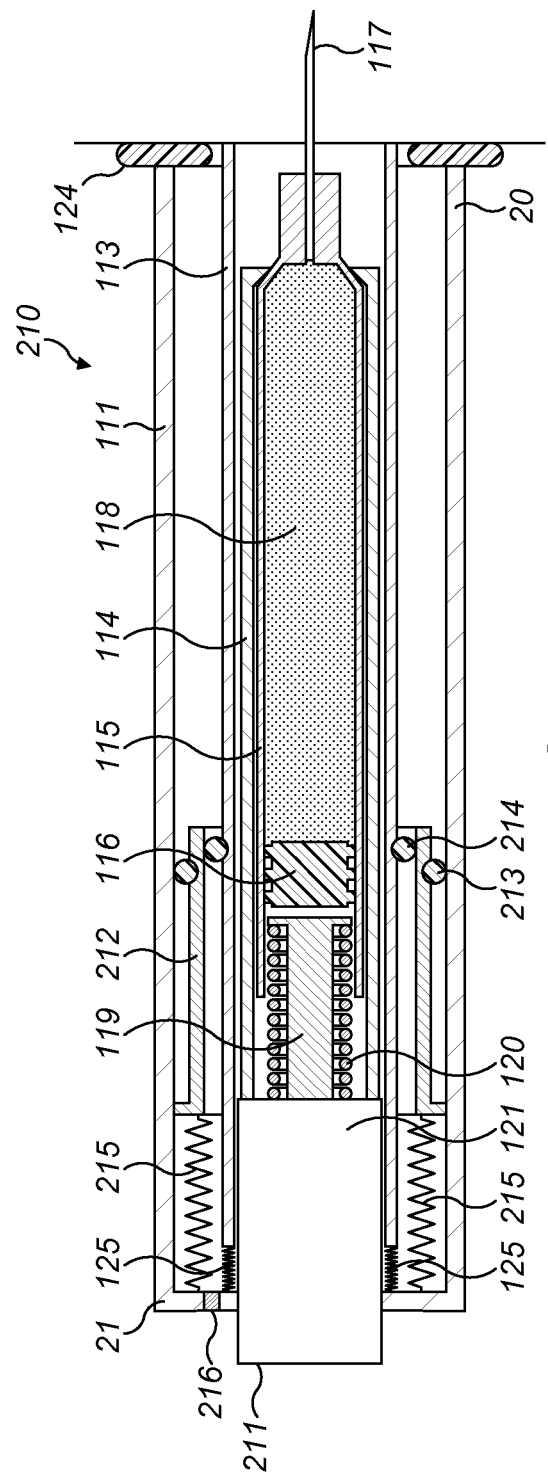
FIG. 8 shows the auto injector of FIG. 6 in a second configuration during an injection process.

A second embodiment of an auto injector 210 is shown in FIGS. 6 to 8, in which features in common with those of the first embodiment retain the same reference numerals. The auto injector 210 comprises an injector housing body 111 (hereafter "body") having a distal region 20 and a proximal region 21. A needle sleeve 113 is provided within the body 111 and is slidable relative to body 111 between an extended position (shown in FIG. 6) and a retracted position (shown in FIGS. 7 and 8). The needle sleeve 113 is a generally tubular structure.

A syringe holder 114 is disposed within the needle sleeve 113 and is configured to receive a syringe 115 or cartridge of liquid medicament 118. The syringe 115 includes a needle 117 at one end and disposed at the distal end 20 of the body 111. The needle 117 extends beyond the distal end 20 of the body. The needle sleeve 113 surrounds the needle 117 in its extended position and the needle 117 is exposed when the needle sleeve 113 is moved to its retracted position.

The syringe 115 includes a stopper 116 at an opposite end to the needle 117 which seals against an inside wall of the syringe 115 to retain the liquid medicament 118 inside the syringe 115. A plunger 119 is disposed adjacent the stopper 116 to move the stopper 116 within the syringe 115 to expel the medicament 118 out of the needle 117. A plunger spring 120 is provided around the plunger 119 and acts to bias the plunger 119 in a direction towards the stopper 116. A power pack 121 (only shown schematically in FIGS. 6 to 8) is connected to the plunger 119 to drive the plunger 119 in a direction towards the stopper 116 assisted by the plunger spring 120. The power pack 121 includes an activation button 211 at a proximal end of the power pack 121 and which extends through the proximal end of the body 111 to be actuated by a patient. The region between the body 111 and the power pack 121/activation button 211 is sealed so that air cannot pass between the body 111 and the power pack 121/activation button 211.

The distal end 20 of the body 111 includes a sealing member 124 in the form of an annular element secured around the end rim of the body 111.

A moveable member in the form of a collar 212 is slidably received within the body 111 and is disposed between the body 111 and the needle sleeve 113. The collar 212 is slidable between a first position (shown in FIGS. 6 and 7) in which it is disposed near the distal end 20 of the body 111, and a second position (shown in FIG. 8) in which it is disposed near, or at least further towards, the proximal end 21 of the body 111. A first annular seal 213, such as an O-ring, is provided around the outer circumference of the collar 212 and is in contact with the inner wall of the body 111. The first annular seal 213 thereby makes a seal between the collar 213 and the body 111. A second annular seal 214, such as an O-ring, is provided around the inner circumference of the collar 212 and is in contact with the outer wall of the needle shield 113. The second annular seal 214 thereby makes a seal between the needle shield 113 and the collar 213.

At least one collar spring 215 is provided extending between the proximal end 21 of the body 111 and the collar 212. In the embodiment shown in FIGS. 6 to 8, two collar springs 215 are shown although there may alternatively be one collar spring or more than two collar springs. For example, a single collar coil spring could be provided surrounding the needle shield 113. The collar springs 215 are configured to bias the collar 212 towards the proximal end 21 of the body 111 and are in a tensioned state as shown in FIGS. 6 and 7, and a state of reduced tension in FIG. 8.

A one-way valve 216 is provided at the proximal end 21 of the body 111 and is configured to allow air to flow out from within the body 111 to outside but does not allow air flow into the interior space defined by the body 111.

At least one sleeve spring 125 is provided between the proximal end 21 of the body and the needle sleeve 113. In the embodiment shown in FIGS. 6 to 8, two sleeve springs 125 are provided, although there may alternatively be one sleeve spring or more than two sleeve springs. The sleeve springs 215 are configured to bias the needle sleeve 113 into the extended position shown in FIG. 6.

A holding mechanism (not shown) is provided between the collar 212 and the needle sleeve 113. The holding mechanism retains the collar 212 in the first position against the force of the collar springs 215 while the needle sleeve 113 is in the extended position. The holding mechanism is configured such that as the needle sleeve 113 is moved into the retracted position, the collar 212 is released and is free to slide within the body under the force of the collar springs 215. This may, for example, be achieved by means of an appropriately shaped pin and slot arrangement on the collar 212 and needle sleeve 113 respectively.

Operation of the auto injector 210 of the second embodiment will now be described. The auto injector 210 is initially in configuration shown in FIG. 6, in which the needle sleeve 113 is in the extended position and the collar 212 is in the first position. The distal end 20 of the auto injector 210 is pressed against the injection site on a patient's body. The needle sleeve 113 is pushed into the body 11 and slides from the extended position to the retracted position, compressing the sleeve springs 125. The needle 117 is thereby exposed and pierces the patient's skin and the sealing member 124 creates an air-tight seal against the patient's skin around the injection site. The auto injector 210 is the in the configuration shown in FIG. 7. As the distal end 20 of the body 111 is thereby sealed closed by the sealing member 124 and the patient's skin, a sealed closed volume is thereby defined within the body 111. As with the first embodiment, the sealing member 124 may be deformable as indicted by the change of shape of the sealing member 124 shown in FIGS. 6 and 7, to help achieve an effective seal against the patient's skin.

Once the needle shield 113 is in the retracted position, the holding mechanism releases the collar 212 which is then drawn towards the proximal end 21 of the body 111 by the collar springs 215. The auto injector 210 is then in the configuration shown in FIG. 8. The first and second annular seals 213, 214 prevent air passing from one end of the body 111 to the other past the collar 212. Therefore, since the sealing member 124 seals against the patient's skin, movement of the collar 212 towards the proximal end 21 of the body 111 enlarges the closed volume within the body 111 between the collar 212 and the patient's skin without allowing air into that volume, creating a reduced pressure in the volume and thereby a suction effect which draws auto injector 210 against the patient's skin and helps support and stabilize the auto injector 210 in position during subsequent medicament delivery process. The sensation of the suction on the patient's skin also serves to give the patient a tactile indication that the auto injector 210 is properly secured in place on their skin and ready to initiate medicament delivery.

The air within the closed space in the body 111 between the collar 212 and the proximal end 21 of the body 111 is allowed to escape via the non-return valve 216. This prevents a build-up of air pressure in this region counteracting the movement of the collar 212 towards the proximal end 21 of the body 111.

The patient then pushes the activation button 211 on the power pack flat 121 which activates the power pack 121 and causes the plunger 119 to be actuated to drive the stopper 116 to deliver the medicament 118 into the patient in a similar manner as described above with reference to the first embodiment.

Once the medicament delivery operation is completed, the patient removes the auto-injector 210 from their skin. This can be achieved by the patient pulling the device from their skin against the suction force creased by the negative pressure.

Once the auto injector 210 is removed from the patient's skin, the needle sleeve 113 then slides into the extended position under the force of the sleeve springs 125 to surround the needle 117.

Although the auto injector 210 of the second is described as having a holding mechanism that automatically releases the collar 212 when the needle sleeve 113 is moved into the retracted position, the auto injector 210 is not limited to this configuration of device and alternative collar release mechanisms are intended within the scope of this disclosure. For example, the auto injector 210 could include a manual activation mechanism for releasing the collar 212 that is actuated by a patient, such as a button on an outer wall of the body 111. That is, the user may manually activate the mechanism that generates the reduced pressure within the body 111.

Although the auto injector 210 of the second embodiment is described as having a non-return valve 216, a variation of the second embodiment may omit the non-return valve, and any build-up of air pressure the region between the collar 212 and the proximal end 21 of the body 111 bay be countered by the force of the collar springs 215.

Although the auto-injector of the first embodiment is described as having first and second coupling elements in the form of the hooks 126 and aperture 127 respectively, these may be reversed such that the moveable cover 122 includes one or more hooks and the needle sleeve 113 includes one or more corresponding apertures. Also, alternative configurations of coupling elements are envisaged, such as, for example, pairs of engageable hooks or a pawl and ratchet mechanism.

Figure 9:
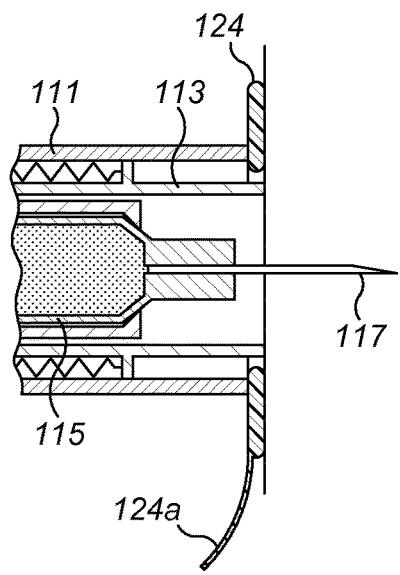
FIG. 9 shows a section of an auto injector of a third embodiment of the invention, similar to the auto injector of the first embodiment shown in FIGS. 2 to 5, in a sealed configuration.
Figure 10:
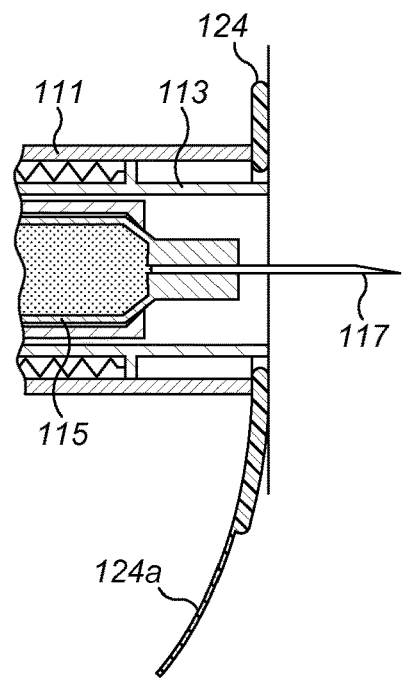
FIG. 10 shows the section of the auto injector of FIG. 9 in an unsealed configuration.

In both the first and second embodiments, variations of auto injector are envisaged which are configured to facilitate equalisation of the reduced pressure within the body 111 with external ambient pressure. One such variation is shown in FIGS. 9 and 10 as a third embodiment, and as a variant of the auto injector 110 of the first embodiment. However, the variant may equally be applicable to the auto injector 210 of the second embodiment. Like features retain the same reference numerals. A difference of the auto injector of the third embodiment is that the sealing member 124 includes a release element in the form of a release tab 124a which extends from the outer edge of the sealing member 124. The patient can pull on the release tab 124a to break the seal between the skin and the sealing member 124 once a medicament delivery process is finished to allow air into the volume within the body 11 and thereby facilitate removal of the auto injector 110 from the patient's skin.

Figure 11:
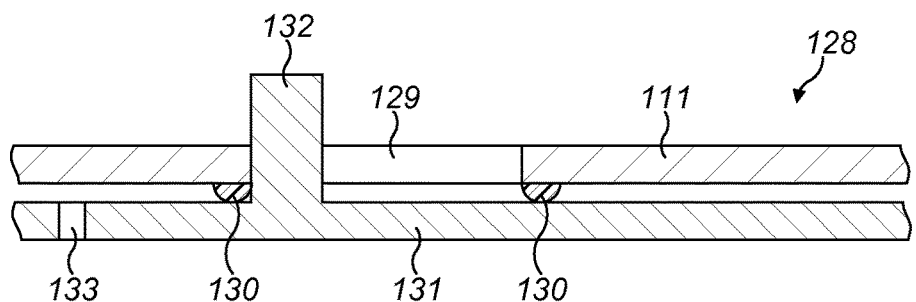
FIG. 11 shows a section of an auto injector of a fourth embodiment of the invention, showing a pressure release mechanism in a sealed configuration.
Figure 12:
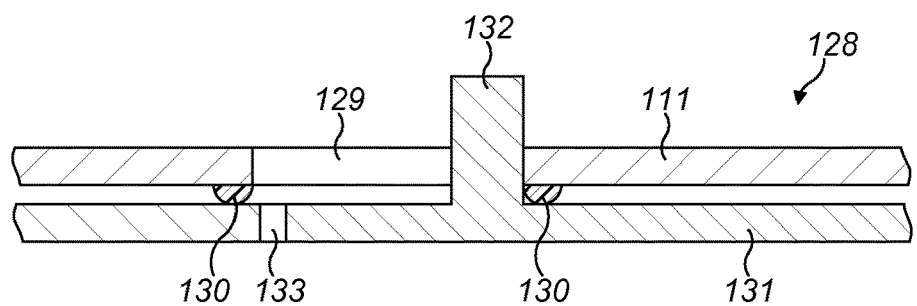
FIG. 12 shows the section of the auto injector of FIG. 11, showing the pressure release mechanism in an unsealed configuration.

A second variation is shown in FIGS. 11 and 12 as a fourth embodiment, and as a variant of the auto injector 110 of the first embodiment. However, the variant may equally be applicable to the auto injector 210 of the second embodiment. Like features retain the same reference numerals. A difference of the auto injector of the fourth embodiment is that the body 111 includes a release element in the form of a vacuum release mechanism 128 which a patient can manually actuate to equalize the reduced pressure within the body 111 with ambient air pressure. The vacuum release mechanism 128 comprises an aperture 129 in the body 111. A resilient seal 130 is provided around the aperture 129 on the inside wall of the body, and may comprise a bead of rubber or similar material, or an O-ring. A plate 131 is slidably mounted over the aperture 129 on the inside of the body 111 and includes a projection 132 extending through the aperture 129. The plate 131 is moveable between a closed position (shown in FIG. 11) and an open position (shown in FIG. 12). A user can manipulate the projection 132 to move the plate 131 between the two positions. The plate 132 is in contact with the resilient seal 130 to prevent the flow of air between the inside of the body 111 and outside the body 11 through the aperture 129. A vent hole 133 is provided in the plate. In the closed position, the vent hole 133 is outside the perimeter of the resilient seal 130, and in the open position the vent hole 133 is within the perimeter of the resilient seal and in fluid communication with the aperture 129. In use, during medicament delivery process when a reduced pressure is maintained within the body 111, the plate 131 is in the closed position to ensure the reduced pressure is maintained. Once a medicament delivery process is finished, the patient can manually actuate the vacuum release mechanism 128 to equalize the reduced pressure within the body 111 with ambient air pressure to allow air into the volume within the body 111 and thereby facilitate removal of the auto injector 110 from the patient's skin. This is done by using the projection 132 to slide the plate 131 into the open position to allow air to flow from outside the body 111 into the body 111 through the aperture 129 and through the vent hole 133.

It will be appreciated that the reduced pressure equalisation configurations of the third and fourth embodiments may equally be applicable to the auto injector 210 of the second embodiment as well as the auto injector 110 of the first embodiment. An advantage of a mechanism to allow a patient to manually equalize the reduced pressure within the body 111 with ambient air pressure is that is provides a manual override function so a patient can quickly remove the auto injector device from their skin if necessary.

It is intended that the auto injector may automatically equalise the reduced pressure within the body 111 with ambient air pressure. Such mechanism may be triggered by the power pack 121 when an injection and medicament delivery process is complete. For example, the body 111 may include a valve with an actuator coupled to the power pack 121, such that the power pack 121 operates the actuator to open the valve. Alternatively, the mechanism may be mechanically triggered at the end of a medicament delivery process is complete. For example, the plunger 119 may include a projection which engages with a valve in the body 111 to open the valve when the plunger reaches a fully extended position when it has pushed the medicament dose out of the syringe 115. An advantage of an automatic pressure equalisation at the end of a medicament delivery process is that it provides feedback to the patient by means of a tactile indication that the medicament delivery process has ended, thereby providing improved device usability.

In some embodiments, as the medicament is delivered to the patient, the stopper 116 slides towards the distal end 20 of the body 111 and leaves behind it a space within the syringe 115 that was previously filled with liquid medicament 118 and which is in fluid communication with the closed space within the body 111 of reduced pressure. This increases the total closed volume within the body but without allowing any more air into the closed volume, and thereby further reduces the pressure within the body 111, increasing the suction effect on the patient's skin. In some cases, this is acceptable and helps achieve the advantages discussed above of the suction effect on the patient's skin. However, it may be that the reduced pressure reaches a level which may be uncomfortable for a patient. Also, the reduced pressure may reach a level where it begins to act against the stopper 116 stalling effective delivery of the medicament 118. Accordingly, some embodiments may include an overpressure valve formed in the body 111. Such overpressure valve may be configured to open when the reduced pressure within the body 111 reaches a threshold level. The overpressure valve may be configured to mechanically open at the threshold level such as by including a valve spring with a predetermined opening tension. Alternatively, the overpressure valve may be electronically actuated. For example, a pressure sensor may be provided within the body, for example within the power pack 121, and the overpressure valve may include an actuator that is operated to open the valve by a signal sent when the pressure sensor detect the threshold pressure has been reached. Such an overpressure valve may be configured to regulate the reduced pressure within the body 111 within a predetermined range of pressure levels. That is, the overpressure valve may not fully equalise the reduced pressure within the body 111 when the overpressure valve is actuated. The overpressure valve may thereby close once the reduced pressure within the body 111 is back to an acceptable level.

It will be appreciated that in the embodiments described above, mechanisms are provided which generate a reduced pressure within the body 111, in addition to any supplementary pressure reduction that may occur by the discharge of medicament 118 from the syringe 115. However, it is intended that variations of the first and second embodiments may be included, in which the reduced pressure within the body 111 is created solely by the stopper 116 sliding towards the distal end 20 of the body 111 and leaving behind it a space within the syringe 115 that was previously filled with liquid medicament 118 and which is in fluid communication with the closed space within the body 111. This increase in the total closed volume within the body without allowing any more air into the closed volume thereby reduces the pressure within the body 111, causing the suction effect on the patient's skin resulting in the above-described advantages. Such an embodiment of auto injector may, for example, be configured as per the auto injector 110 of the first embodiment shown in FIGS. 2 to 5, but in which the moveable cover 122 and flexible cap 123 are omitted and the body 111 simply has a closed proximal end 21 which is fixed. Such a proximal end may include an activation button 211 from the power pack 121 as per the second embodiment. Alternatively, such an embodiment of auto injector may, for example, be configured as per the auto injector 210 of the second embodiment shown in FIGS. 6 to 8, but in which the collar 212 and collar springs 215 are omitted. In both cases, it would be necessary for the end of the syringe 115 near the proximal end 21 of the body 111 to be open and in fluid communication with the closed interior space within the body 111.

Although the first and second embodiments of auto injector are described as including a power pack 121 to actuate the plunger 119, the auto injector is not intended to be limited to auto injectors having a power pack and alternatively, embodiments of the auto injector may include a plunger spring 120 without a power pack 121 to drive the plunger 119. In some embodiments, it will therefore be the case that the plunger spring 120 drives both the plunger 119 to deliver the liquid medicament from the syringe 115 into the patient and also generates the reduced pressure within the body 111. In such embodiments, the plunger spring 120 may be configured to provide sufficient force to perform both functions. The actuation of the plunger in such embodiments may be effected by a mechanical release mechanism, for example.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated. The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis. Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the APIs, substances, formulations, apparatuses, methods, systems and embodiments described herein may be made without departing from the full scope and spirit of the present invention, which encompass such modifications and any and all equivalents thereof.

The invention claimed is:

1. An auto-injector device for delivering a liquid medicament, comprising:
an injector body having a proximal end and a distal end;
a syringe received in the injector body;
a needle disposed in a first end of the syringe to extend toward an opening in the distal end of the injector body; and
a sealing element disposed at the distal end of the injector body, the sealing element configured to form a seal against a patient's skin and thereby define a closed volume within the injector body in use,
wherein the auto-injector is configured to generate a reduced pressure within the closed volume to draw the auto-injector device against the patient's skin, and wherein the auto-injector device comprises a pressure reducing mechanism configured to generate the reduced pressure within the injector body during an injection process, the pressure reducing mechanism comprising a moveable member which is moveable in a longitudinal direction of the injector body from a first position in a direction towards the proximal end of the injector body to a second position and which is configured such that movement of the moveable member from the first position to the second position enlarges the closed volume within the injector body to generate the reduced pressure within the closed volume, and wherein the pressure-reducing mechanism includes a biasing element configured to bias the moveable member into the second position.

2. The auto-injector device according to claim 1, wherein the syringe comprises a second end opposite the first end, and wherein the second end is open and in fluid communication with the closed volume within the injector body, and wherein the pressure reducing mechanism comprises the syringe.

3. The auto-injector device according to claim 1, further comprising a needle sleeve moveable between an extended position in which the needle sleeve extends from the distal end of the injector body and surrounds the needle and a retracted position in which the needle sleeve is retracted into the injector body to expose the needle.

4. The auto-injector device according to claim 3, comprising a holding mechanism configured to hold the moveable member in the first position and to release the moveable member when the needle sleeve moves from the extended position to the retracted position.

5. The auto-injector device according to claim 3, wherein the needle sleeve comprises a first coupling element, and the moveable member comprises a second coupling element, and wherein the first and second coupling elements engage when the needle sleeve moves to the retracted position.

6. The auto-injector device according to claim 1, wherein the injector body comprises a non-return valve configured to allow air to flow out of the injector body but to prevent air from flowing into the injector body from outside the device.

7. The auto-injector device according to claim 1, wherein the sealing element comprises a resilient annular sealing member disposed around a rim of the injector body at the distal end.

8. The auto-injector device according to claim 1, comprising a release element operable to equalize the reduced pressure within the closed volume with air pressure outside the injector body.

9. The auto-injector device according to claim 8, wherein the release element comprises a release valve, and the auto-injector device comprises a release mechanism configured to automatically operate the release valve when a medicament delivery process is complete.

10. The auto-injector device according to claim 8, wherein the release element is manually operable to allow a user to actuate the release element.

11. The auto-injector device according to claim 1, wherein the syringe contains a liquid medicament.

12. The auto-injector device according to claim 1, wherein the syringe contains a cartridge of liquid medicament.

13. A method of operation of an auto-injector device for delivering a liquid medicament, the auto-injector device comprising:
   an injector body having a proximal end and a distal end;
   a syringe received in the injector body;
   a needle disposed in a first end of the syringe to extend toward an opening in the distal end of the injector body;
   a sealing element disposed at the distal end of the injector body; and
   a pressure-reducing mechanism comprising a moveable member which is moveable in a longitudinal direction of the injector body from a first position in a direction towards the proximal end of the injector body to a second position, wherein the pressure-reducing mechanism includes a biasing element configured to bias the moveable member into the second position, wherein the method comprises:
   placing the distal end of the injector body against a patient's skin;
   making a seal between the injector body and the patient's skin with the sealing element and thereby defining a closed volume within the injector body; and
   moving the moveable member from the first position to the second position to enlarge the closed volume within the injector body, thereby generating a reduced pressure within the closed volume to draw the auto-injector device against the patient's skin.

14. The method according to claim 13, wherein the auto-injector device comprises a needle sleeve, and the method comprises moving the needle sleeve from an extended position in which the needle sleeve extends from the distal end of the injector body and surrounds the needle to a retracted position in which the needle sleeve is retracted into the injector body to expose the needle.

15. The method according to claim 14, comprising pressing the distal end of the injector body against the patient's skin to move the needle sleeve from the extended position to the retracted position.

16. The method according to claim 14, comprising contacting the sealing element with the patient's skin in response to moving the needle sleeve from the extended position to the retracted position to make the seal between the injector body and the patient's skin.

17. The method according to claim 14, wherein the auto-injector device comprises a holding mechanism, and the method comprises holding the moveable member in the first position with the holding mechanism and releasing the moveable member from the holding mechanism in response to moving the needle sleeve from the extended position to the retracted position.

18. The method according to claim 14, wherein the needle sleeve comprises a first coupling element, the moveable member comprises a second coupling element, and the method comprises engaging the first and second coupling elements in response to moving the needle sleeve to the retracted position.

19. The method according to claim 13, wherein the auto-injector device comprises a release element, and the method comprises operating the release element to equalize the reduced pressure within the closed volume with air pressure outside the injector body.

20. The method according to claim 19, wherein the release element comprises a release valve, the auto-injector device comprises a release mechanism, and the method comprises actuating the release mechanism to automatically operate the release valve when a medicament delivery process is complete.

* * * * *